United States Patent
Ory et al.

(10) Patent No.: US 9,186,235 B2
(45) Date of Patent: *Nov. 17, 2015

(54) PROSTHETIC KNIT WITH GRIP PROPERTIES, METHOD FOR ITS PRODUCTION, AND REINFORCEMENT IMPLANT FOR TREATMENT OF PARIETAL DEFECTS

(75) Inventors: Francois-Regis Ory, Fontaines Saint Martin (FR); Michel Therin, Lyons (FR); Alfredo Meneghin, Lyons (FR)

(73) Assignee: Sofradim Production (FR)

( * ) Notice: Subject to any disclaimer, the term of this patent is extended or adjusted under 35 U.S.C. 154(b) by 1897 days.

This patent is subject to a terminal disclaimer.

(21) Appl. No.: 12/032,750

(22) Filed: Feb. 18, 2008

(65) Prior Publication Data

US 2008/0195231 A1    Aug. 14, 2008

Related U.S. Application Data

(63) Continuation of application No. 10/258,019, which is a continuation of application No. PCT/FR01/01234, filed on Apr. 20, 2001, now Pat. No. 7,331,199.

(30) Foreign Application Priority Data

Apr. 20, 2000 (FR) ..................................... 00 05124

(51) Int. Cl.
*D04B 21/12* (2006.01)
*A61F 2/00* (2006.01)

(52) U.S. Cl.
CPC ............. *A61F 2/0063* (2013.01); *D04B 21/12* (2013.01); *A61F 2002/0068* (2013.01); *A61F 2220/0016* (2013.01); *A61F 2220/0083* (2013.01); *D10B 2501/0632* (2013.01); *D10B 2509/08* (2013.01)

(58) Field of Classification Search
CPC ............ D04B 1/02; D04B 1/04; D04B 21/02; D04B 21/04; A61F 2002/0065
USPC ........ 66/170, 191, 192, 195, 198; 623/14, 15; 606/151, 154
See application file for complete search history.

(56) References Cited

U.S. PATENT DOCUMENTS 3,320,649 A * 5/1967 Naimer ........................... 28/161
3,718,725 A * 2/1973 Hamano ........................ 264/163
4,338,800 A * 7/1982 Matsuda ......................... 66/194

(Continued)

FOREIGN PATENT DOCUMENTS

DE   198 32 634 A1   1/2000
EP   0 276 890 A2   8/1988

(Continued)

OTHER PUBLICATIONS

European Search Report for EP 09174771.7-2314 date of completion is Nov. 23, 2009 (7 pages).

*Primary Examiner* — Danny Worrell

(57) ABSTRACT

A prosthetic knit for medical or surgical use which has a structure made of monofilament and/or multifilament yarn which is biocompatible and optionally partially bioabsorbable.
According to the invention, this knit comprises a monofilament sheet forming, on one face of the knit, spiked naps which protrude perpendicularly with respect to said sheet, that is to say naps each having a substantially rectilinear body and, at the free end of this body, a head of greater width than that of this body.

15 Claims, 4 Drawing Sheets

(56) References Cited

U.S. PATENT DOCUMENTS

| | | | |
|---|---|---|---|
| 4,391,106 A * | 7/1983 | Schafer et al. | 602/44 |
| 4,476,697 A * | 10/1984 | Schafer et al. | 602/44 |
| 4,709,562 A | 12/1987 | Matsuda | |
| 5,254,127 A * | 10/1993 | Wholey et al. | 606/153 |
| 5,254,133 A | 10/1993 | Seid | |
| 5,330,445 A * | 7/1994 | Haaga | 604/265 |
| 5,356,432 A | 10/1994 | Rutkow et al. | |
| 5,569,273 A * | 10/1996 | Titone et al. | 606/151 |
| 5,761,775 A * | 6/1998 | Legome et al. | 24/450 |
| 5,906,617 A * | 5/1999 | Meislin | 606/331 |
| 6,039,741 A * | 3/2000 | Meislin | 606/90 |
| 6,110,210 A * | 8/2000 | Norton et al. | 623/17.16 |
| 6,120,539 A * | 9/2000 | Eldridge et al. | 623/11.11 |
| 6,408,656 B1* | 6/2002 | Ory et al. | 66/195 |
| 6,443,964 B1* | 9/2002 | Ory et al. | 606/151 |
| 6,596,002 B2* | 7/2003 | Therin et al. | 606/151 |
| 6,638,284 B1* | 10/2003 | Rousseau et al. | 606/151 |
| 6,971,252 B2* | 12/2005 | Therin et al. | 66/170 |
| 7,213,421 B2* | 5/2007 | Shirasaki et al. | 66/193 |
| 7,331,199 B2* | 2/2008 | Ory et al. | 66/170 |
| 7,614,258 B2* | 11/2009 | Cherok et al. | 66/192 |
| 2006/0281967 A1* | 12/2006 | Meneghin et al. | 600/37 |
| 2008/0195231 A1* | 8/2008 | Ory et al. | 623/23.72 |
| 2008/0208360 A1* | 8/2008 | Meneghin et al. | 623/23.75 |
| 2009/0036907 A1* | 2/2009 | Bayon et al. | 606/151 |
| 2010/0049222 A1* | 2/2010 | Cherok et al. | 606/151 |

FOREIGN PATENT DOCUMENTS

| | | |
|---|---|---|
| EP | 0 719 527 A1 | 7/1996 |
| EP | 0 797 962 B1 | 10/1997 |
| EP | 0 827 724 A2 | 3/1998 |
| EP | 0 836 838 B1 | 4/1998 |
| FR | 2 744 906 A1 | 8/1997 |
| FR | 2 766 698 A1 | 2/1999 |
| FR | 2 779 937 A1 | 12/1999 |
| WO | WO 95/07666 | 3/1995 |
| WO | WO 96/03091 | 2/1996 |
| WO | WO 96/41588 | 12/1996 |

* cited by examiner

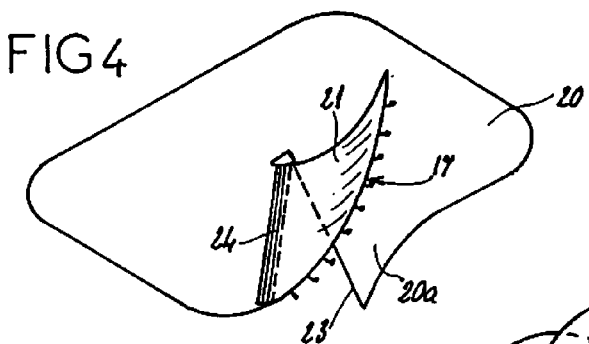
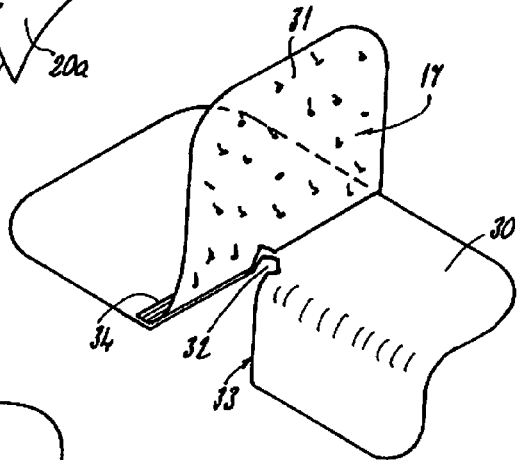
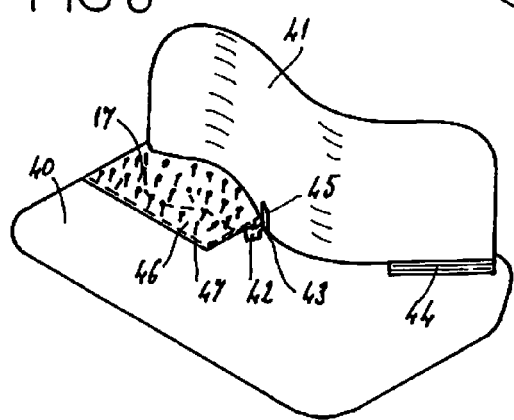
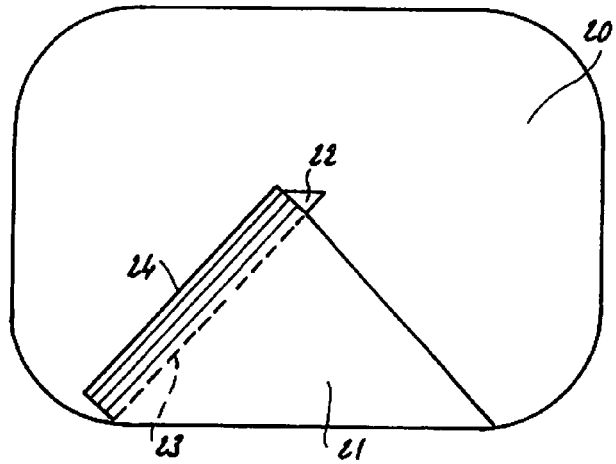

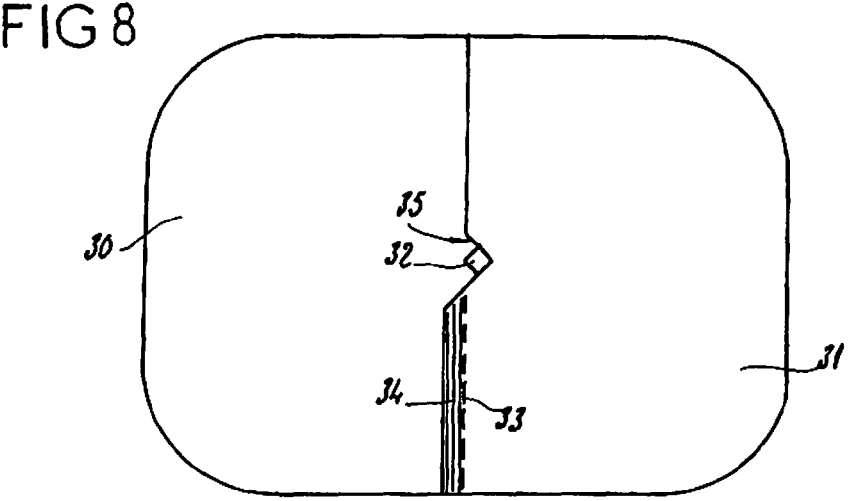
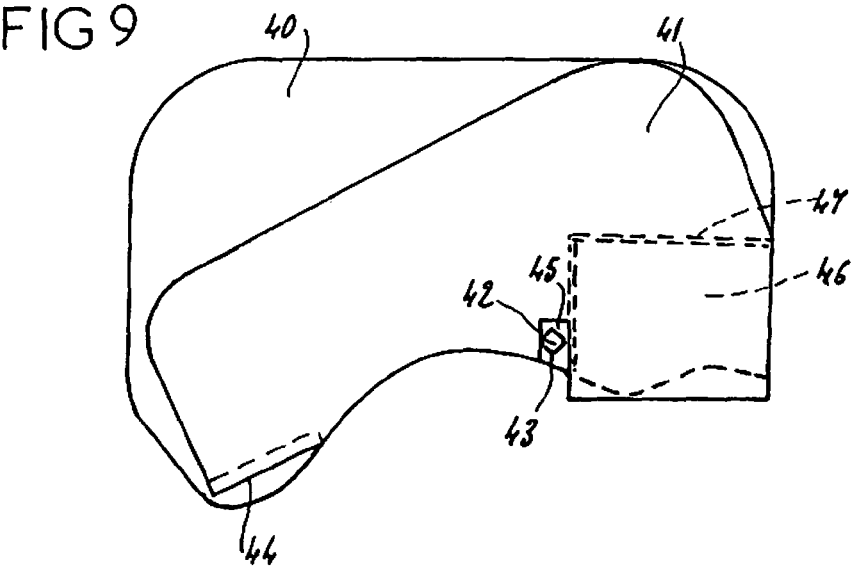

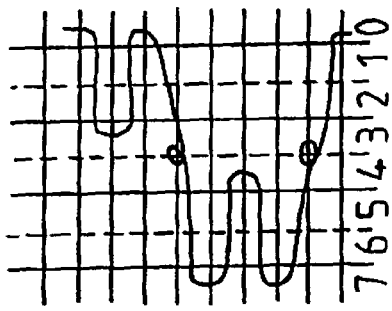
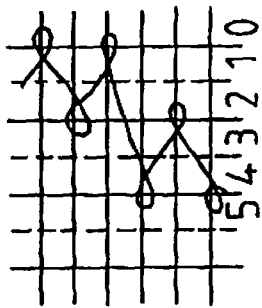
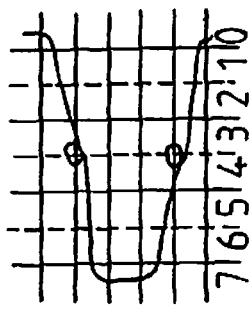
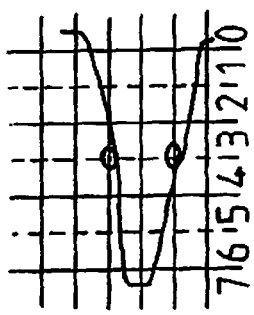
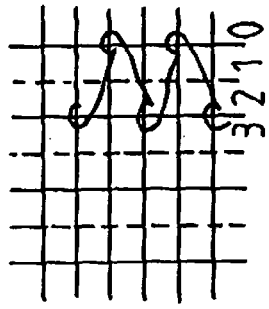

PROSTHETIC KNIT WITH GRIP PROPERTIES, METHOD FOR ITS PRODUCTION, AND REINFORCEMENT IMPLANT FOR TREATMENT OF PARIETAL DEFECTS

CROSS-REFERENCE TO RELATED APPLICATIONS

This application is a continuation and claims the benefit of U.S. patent application Ser. No. 10/258,019 filed Jan. 7, 2003, now U.S. Pat. No. 7,331,199, (the entire content of which is incorporated by reference herein), which is a national stage application of PCT/FR01/01234 filed Apr. 20, 2001 which claims priority to French patent application No. 00/05124 filed Apr. 20, 2000.

The invention relates to a prosthetic knit with grip properties, to a method for producing this prosthetic knit, and to a reinforcement implant formed with this prosthetic knit allowing treatment of parietal defects.

BACKGROUND OF THE INVENTION

In the treatment of parietal insufficiencies (hernias and eventrations for the most part), the aim of the reinforcement is to give a permanent mechanical support to the surgical reconstruction. The reinforcement is all the more effective, and its local tolerance all the better, if it integrates in the tissue intimately and at an early stage. To achieve intimate and early integration without formation of a peripheral fibrous shell, the macroporosities of the implant must be as widely open as possible to the outside and the elasticity of the reinforcement must allow it to follow the physiological deformations of the wall. The limits are fixed by the mechanical resistance of the textile, which must be greater than 10 decanewtons in the standardized ISO5081 test, by the maneuverability by the surgeon, and by the impossibility of hernia recurring through the pores of the tissue which must be a maximum of 7 to 10 millimetres in diameter, for example.

DESCRIPTION OF THE PRIOR ART

The concept of a tissue reinforcement of the abdominal wall in the form of a knitted textile has been known for decades in the scientific literature. A number of technical solutions have been described, in particular in the following documents: U.S. Pat. No. 5,569,273, WO 96/03091, EP 0 797 962, FR 2 766 698. These all have in common the knitting of monofilaments or multifilaments of polypropylene or polyester.

In a known manner, such tissue reinforcements, also called prosthetic fabrics or knits, have to meet a number of requirements, and in particular they have to have a mechanical strength in at least two perpendicular directions, be biocompatible, flexible and conformable, while having a certain elasticity, in at least one direction, be porous and transparent, be able to be sutured and recut, while at the same time being non-tear and runproof, and, finally, they must be sterilizable and durable. In general, these reinforcements are knitted and made up of several sheets of interlaced yarns forming a structure which is referred to as being three-dimensional, since it has a certain thickness when flat.

Specific forms of these textiles which are able to conform, on the one hand, to the anatomy of the inguinal region and, on the other hand, to the surgical technique employed have also been known for many years, both for posterior access routes (EP 0 836 838, WO 95/07666, WO 96/41588) and for anterior access routes (U.S. Pat. No. 5,356,432, EP 0 827 724). While in general the reinforcements designed for the posterior access routes are of large dimensions and require only a small number of fixing points, the reinforcements designed for the anterior access routes are of smaller dimensions, are slotted (in advance or extemporaneously) to surround the spermatic cord and therefore require relatively extensive fixing, on the one hand in order to close the slit on itself, and on the other hand to oppose the intra-abdominal forces of extrusion and, finally, to guarantee rapid integration with the peripheral tissues.

SUMMARY OF THE INVENTION

The invention more especially concerns reinforcement implants comprising two elements joined together by stitching or welding and forming two flaps which superpose each other, at least locally. The object of the invention is to make available a knit with grip properties which satisfies the specific requirements of prosthetic knits, as set out above, but which confers various advantages on any reinforcement implant made with said knit, namely possible omission of any additional operation for joining the two elements together, simplicity of use, speed and safety of placement by the practitioner, and efficacy of the functional repair.

The present invention proposes a prosthetic knit for medical or surgical use whose structure is made up of monofilament and multifilament yarn which is biocompatible and optionally partially bioabsorbable.

According to the invention, this prosthetic knit comprises a monofilament sheet forming, on one face of the knit, spiked naps which protrude perpendicularly with respect to said sheet, that is to say naps each having a substantially rectilinear body and, at the free end of this body, a head of greater width than that of this body.

This knit can in particular be obtained using a thermofusible monofilament to constitute said monofilament sheet, forming outer loop-shaped meshes in said sheet, then partially fusing said monofilament.

The length of the spiked naps is defined so as to penetrate and fasten in the textile structure of the knit in a limited manner, that is to say without emerging from the other face, for example when the grip side of a knit according to the invention comprising said spiked naps is applied against a non-grip face, not comprising said naps, of the same knit or of a different knit.

Preferably, the monofilament forming the spiked naps has a diameter of over 0.10 mm, and/or each spiked nap has a length of between 1 mm and 2 mm, and/or the density of the spiked naps is between 50 and 90 naps per square centimeter.

Moreover, in a preferred manner, the textile structure of the knit comprises or defines on its two faces, including the one with the spiked naps, open pores which for example have a diameter of between 1 and 3 mm. By way of example, this structure comprises several sheets of interlaced yarns which together form a three-dimensional structure. In the latter case, the three-dimensional structure is composed, for example, of three sheets, namely:
an intermediate sheet of yarn distributed to form a zigzag openwork pattern between the columns of meshes,
a front sheet of yarns distributed to form a chain stitch, and
a rear sheet of monofilament placed in partial weft under the chain stitch and "thrown onto" the needle not forming a chain stitch, this sheet comprising the spiked naps.

When a grip-type knit according to the invention is applied, with spiked naps to the front, onto a napless prosthetic knit, the spiked naps engage in the meshes and between the multifilament yarns of the reinforcement knit and lock the grip-type knit onto the other knit. This locking, effective even in a liquid environment, is sufficient to secure the closure of a slit, if one exists, and to offer mechanical resistance to tangential stresses, while at the same time permitting unfastening of the grip-type knit in order to adjust its position in relation to the element lying underneath.

The invention also concerns a method for production of this grip-type knit defined above by way of example and comprising three sheets, namely intermediate, front and rear.

This method comprises:
(i) a phase of production of a looped knit on a warp knitting machine, with at least three sheets of yarns and the same number of guide bars, namely:
 a rear bar which is threaded, one guide full and one guide empty, with the monofilament forming the spiked naps,
 an intermediate bar which is threaded, one guide full, three guides empty, forming a light ground texture which is openworked and stable in width,
 a front bar which is threaded, one guide full, one guide empty, these three bars working according to the following chart:

| | Warp | |
|---|---|---|
| Rear bar I | Intermediate bar II | Front bar III |
| | Raschel | |
| Front bar I | Intermediate bar II | Rear bar III |
| 7 | 3 | 1 |
| 7 | 2 | 0 |
| — | — | — |
| 3 | 4 | 0 |
| 4 | 5 | 1 |
| — | — | — |
| 0 | 1 | |
| 0 | 0 | |
| — | — | |
| 4 | 2 | |
| 3 | 3 | |
| | — | |
| | 1 | |
| | 0 | |
| | — | |
| | 4 | |
| | 5 | |

(ii) a phase of thermosetting of the looped knit, and
(iii) a phase of transformation of the loops to spiked naps by pressing the knit flat as it crosses a cylinder maintained at a temperature which results in melting of the loops and formation of the spikes.

The invention also concerns all use of a knit, as defined above, for obtaining a prosthetic article for medical or surgical use, for example a prosthetic implant for tissue reinforcement.

The invention thus also concerns a prosthetic implant for tissue reinforcement whose main characteristic is that it is formed at least in part by a knit according to the invention.

By way of example, such a prosthetic implant comprises a grip part or element, for example a flap, one of whose faces, called the grip face, comprises spiked naps arranged and/or disposed to penetrate in a limited manner and fasten within the thickness of the textile structure of another part or other element, for example a non-grip part or element, which may belong to the same implant or to another prosthetic article or part, and this when the grip face of the grip element, that is to say the element comprising the spiked naps, is arranged against a non-grip face, that is to say without spiked naps, of said other element.

The whole of the grip element is preferably made of a knit according to the invention.

The grip element is preferably connected to the rest of the implant via a connection zone, for example by stitching or welding.

Preferably, and as will be described below, the grip element and said other, non-grip element belong to the same implant and are, for example, two flaps which superpose each other locally. In the latter case, the two elements, namely grip element and non-grip element, are arranged and/or disposed in relation to each other in such a way that, in their gripped position, the spiked naps remain within the perimeter or contour of the implant, so that the spiked naps cannot subsequently come into contact with the surrounding biological tissues.

In the reinforcement implant according to the invention, one of the elements is formed by a prosthetic knit composed of at least three sheets, one of which is made of monofilament forming spiked naps which protrude on one face in the direction of the other element and by a length which is less than the thickness of the knitted structure of this other element, this element with spiked naps being connected to the other prosthetic knit element, which is without spiked naps, by way of a connection zone, formed by stitching or welding, disposed in the zone in which the two elements are superposed.

By virtue of this arrangement, the spiked naps of the grip-type knit are located in the zone of superposition of the two elements of the implant and cannot in any circumstance irritate the surrounding biological tissues.

DESCRIPTION OF THE DRAWINGS

Other characteristics and advantages will become evident from the following description in which reference is made to the attached diagrammatic drawing representing, by way of example, an embodiment of the grip-type knit and several embodiments of the implants which use it.

FIGS. 4 through 6 are perspective views showing three embodiments of parietal reinforcements, with their grip flap moved aside to show the structure and form of the implant, FIGS. 7 through 9 are top views of the implants from FIGS. 3 through 5, with the flaps folded down, FIGS. 10 through 14 are views of various weaves which can be used in an alternative manner to obtain the grip type knit according to the invention.

DESCRIPTION OF PREFERRED EMBODIMENTS

The grip-type knit according to the invention is made on a warp knitting machine, of the tricot or Raschel type, with at least three sheets or warps of yarn and as many guide bars.

Figure 1:
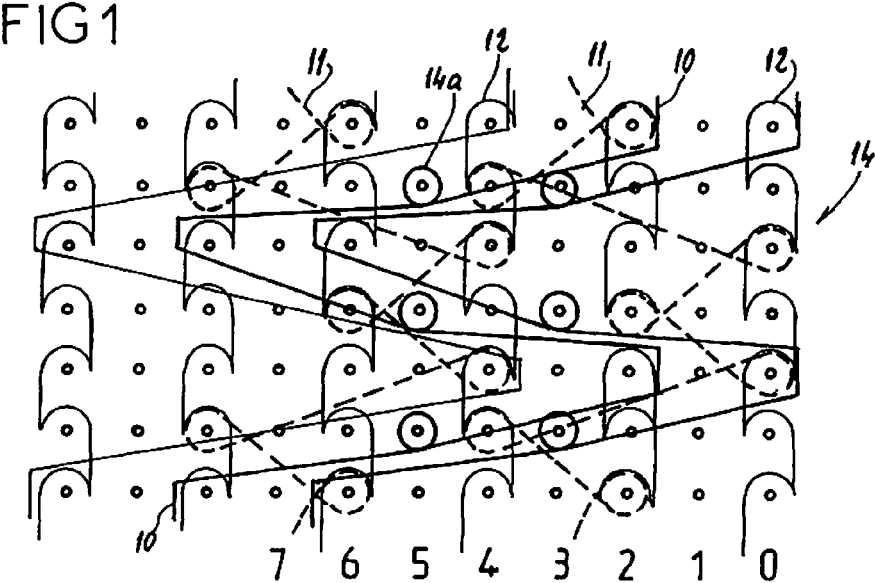
FIG. 1 is a diagram showing, by way of example, the weave of the three sheets forming the grip-type knit.

The rear bar is threaded, one guide full and one guide empty, with monofilament of a biocompatible hot-melt polymer, for example polypropylene, having a diameter of over 0.10 millimeter. In practice, this diameter is between 0.14 and 0.18 millimeter and is of the order of 0.15 millimeter. This yarn is represented by reference number 10 and in a solid line in FIG. 1.

The intermediate bar is threaded, one guide full, three guides empty, with multifilament polyester, but it can also be threaded with monofilament polyester or monofilament or multifilament polypropylene. This yarn is represented by a broken line and by reference number 11 in FIG. 1. The intermediate bar works in such a way as to obtain a zigzag openwork pattern between the columns of meshes.

Finally, the front bar is threaded, one guide full, one guide empty, and works in chain weave with a multifilament or monofilament yarn of polyester or polypropylene and, for example, a multifilament polyester yarn. This yarn is represented by a thin line and by reference number 12 in FIG. 1. The chain stitch imprisons the monofilament 10 and maintains the knit in length while contributing to the formation of the knit with the intermediate sheet formed by the yarn 11. The different yarns are worked according to the following chart:

| Warp | | |
|---|---|---|
| Rear bar I | Intermediate bar II | Front bar III |
| | Raschel | |
| Front bar I | Intermediate bar II | Rear bar III |
| 7 | 3 | 1 |
| 7 | 2 | 0 |
| — | — | — |
| 3 | 4 | 0 |
| 4 | 5 | 1 |
| — | — | — |
| 0 | 1 | |
| 0 | 0 | |
| — | — | |
| 4 | 2 | |
| 3 | 3 | |
| | — | |
| | 1 | |
| | 0 | |
| | — | |
| | 4 | |
| | 5 | |

The rear bar places the yarn in partial weft under the chain stitch and "thrown" onto the needle not forming a chain stitch. For this reason, at the next row, the needle not forming a chain stitch not being supplied permits escape of the monofilament mesh which forms a loop 14a projecting from the front face of the knit.

The threading—one guide full, three guides empty—in the intermediate bar, associated with the displacement, makes it possible to form a light ground texture, stable in width, and openworked to permit good tissue integration.

The knit 14 thus obtained is provided with loops 14a (FIG. 2) which are perpendicular to one of its faces and of which the rigidity and the hold at a right angle are obtained by the rigidity or nerve of the monofilament employed. This rigidity is necessary for the subsequent formation of the spiked naps which ensure the grip function.

In another embodiment, the monofilament forming the loops and subsequently the spiked naps is made of bioabsorbable hot-melt material chosen, for example, from the group consisting of the polymers of p-dioxanone, polyglycolides, polyorthoesters, polymers of trimethylene carbonate, stereocopolymers of L-lactic acid and D-lactic acid, homopolymers of L-lactic acid, copolymers of lactic acid and a compatible comonomer, such as derivatives of alpha-hydroxy acids.

Figure 2:
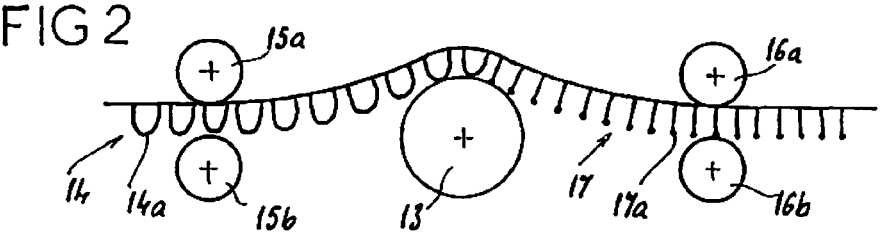
FIG. 2 is a diagrammatic side view of an embodiment of the device permitting formation of the spiked naps.
Figure 3:
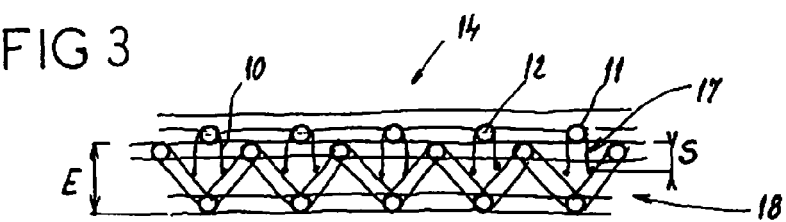
FIG. 3 is a diagrammatic side view illustrating, in an unconventional manner, the interpenetration of the respective structures of the grip-type knit and of the prosthetic knit in which this fastens.

On leaving the loom, the knit 14 is subjected to a thermosetting operation which stabilizes it in length and in width, then it is subjected to a phase of formation of the spiked naps consisting, as is shown in FIG. 2, in passing it over a cylinder 13 containing an electrical heating resistor. The knit 14 is pressed flat on the cylinder 13 by two pairs of rollers, upstream 15a, 15b and downstream 16a, 16b, respectively, which are vertically displaceable for controlling this pressing force.

This control as well as that of the temperature of the resistor placed in the cylinder 13 and of the speed of movement of the sheet 14 across the cylinder make it possible to melt the head of each of the loops 14a so that each loop 14a forms two spiked naps 17.

Each spiked nap 17 thus has a substantially rectilinear body protruding perpendicularly with respect to the monofilament sheet 10 and, at the free end of this body, a head 17a of greater width than that of this body. This head 17a has a generally spheroidal shape or a mushroom shape.

The length S of the naps 17, measured from the face from which they project perpendicularly as far as the summit of the head 17a, is determined such that it is smaller than the thickness E of the knitted structure 18 in which they are to penetrate and fasten themselves, and it is between 1 and 2 millimeters.

The knitted structure 18 with which the grip-type knit 14 cooperates is a prosthetic fabric satisfying the requirements set out in the preamble and is in particular a three-dimensional openworked knit with two porous faces which are connected by connecting yarns. It is, for example, formed using the knit defined in French patent No. 2 766 698.

When the grip-type knit 14 is engaged, with the spiked naps 17 leading, in the direction of the prosthetic knit 18, the spiked naps 17 fit into the meshes of the knit 18 and fasten between the filaments of these meshes, but without emerging from the knit 18 which would bring about the risk of irritating the surrounding biological tissues.

The density of the spiked naps 17 depends on the gage used and on the nerve and rigidity of the monofilament 10. It is between 50 and 90 naps per $cm^2$. This density is sufficient to ensure gripping, while also permitting unfastening of the two knits 14 and 18.

Such a knit is of advantage, for example, for producing reinforcement implants which are to be folded back or secured to themselves, in particular parietal implants.

The implant shown in FIGS. 4 through 7, intended for reinforcing the inguinal region via a posterior access route, is composed of an element 20 made of prosthetic knit 18, and consequently openworked and porous, and of a grip element 21 made of the grip-type knit 14 according to the invention. The element 20 has the general shape of a rectangle with rounded edges and comprises a central opening 22, here of triangular shape, into which there opens a slit 23 delimiting the posterior flap 20a of the implant. The edge of the slit opposite the flap 20a supports the zone of connection 24, by welding or stitching, of the element 21 which has a triangular shape forming an anterior flap which is superposed totally on the posterior flap, or other non-grip element 20a. FIG. 4 shows that the spiked naps 17 are directed so as to protrude in the direction of the flap 20a.

In the reinforcement implant shown in FIGS. 5 and 8, likewise intended for reinforcing the inguinal region via a posterior access route, the element 30 made of standard prosthetic fabric 18 has the shape of a rectangle with rounded edges and comprises a central opening 32, of square shape, communicating with the outside via a slit 33. The grip element 31 extends over half of the element 30 and is fixed to the latter at a zone of connection 34, by welding or stitching. So as not to obstruct the opening 32 when folded down on the element 30, the element 31 comprises a notch 35 in proximity to this opening. FIG. 5 shows that, as in the preceding embodiment, the spiked naps 17 of the element 31 are turned in the direction of the flap 30 onto which they are to be folded.

It will be noted that, in these implants, the elements 21 and 31 made of grip-type knit 14 and intended to be folded down onto the element 20 and 30, respectively, made of non-grip knit 18 are configured so that, after they have been folded down, they are inscribed within the shape of the element 20 and 30, in such a way that in no circumstance can the spiked naps 17 come into contact with the surrounding biological tissues.

The implant shown in FIGS. 6 and 9, having the same use as the preceding implants but being designed for a different surgical technique, is composed of two elements 40 and 41 made of non-grip prosthetic fabric 18. These two elements have configurations which are defined as a function of the anatomy and they are connected to one another by stitching 44. The element 40 comprises an opening 42, of square shape and continued by a slit 43, and the element 41 comprises a notch 45 in its part intended to be applied on the opening 42 and the slit 43. The two elements 40 and 41 are connected via a piece 46 of grip-type knit 14 which is connected to the element 41 by stitching 47. This piece is arranged with the spiked naps 17 protruding from the anterior face of the element 40.

In an implant according to the present invention, the grip element can be made integrated in or attached to the textile structure of said implant.

All of these implants, intended to be positioned via a posterior access route, pass very easily through a trocar by being folded with the spiked naps protruding outward. Once in place, the elements of the implant are unfolded to adjust the position of the implant, but also to pass an organ, for example the spermatic cord, through the opening 22, 32 or 42. When the implant is correctly deployed and well positioned, the folding of the element 21, 31 or 41 down onto the other element ensures, by means of the self-gripping nature of the spiked naps 17, the self-gripping of these elements and the reinforcement of the weakest inguinal region, namely the fascia transversalis.

If necessary, the surgeon can separate the gripped flaps and then resecure them.

By virtue of its design which satisfies the requirements of prosthetic reinforcements, the grip-type knit is without consequence on tissue restoration. If the monofilament constituting the spiked naps is made of bioabsorbable material, the spiked naps disappear when tissue restoration is sufficient to ensure connection of the elements of the implant.

It goes without saying that the invention is not limited to the embodiment described above by way of example, and instead it encompasses all the alternative embodiments thereof.

Thus, the knit 14 can be absorbable or non-absorbable or can be partially absorbable.

The different materials-which can be used for the parts of the implant are indicated below, all the combinations of materials for the different parts of one and the same implant being possible:

yarn for formation of the loops giving rise to the spiked naps: monofilament polypropylene or monofilament lactic acid polymer;

warp of the knit: monofilament polypropylene, multifilament polypropylene, multifilament lactic acid polymer or multifilament polyethylene terephthalate;

weft of the knit: monofilament polypropylene, multifilament polypropylene, multifilament lactic acid polymer or multifilament polyethylene terephthalate;

yarn forming the anchoring loops of the spiked naps and/or constituting the prosthetic knit on which the knit 14 is applied: multifilament polypropylene, multifilament lactic acid polymer or multifilament polyethylene terephthalate.

Other types of weaves than those described above may be envisaged. Thus, the rear bar can move in accordance with one of the weaves indicated below, depending on the desired density of the spiked naps:

00/43/77/34/00 (see FIG. 10);
00/43/77/77/34/00 (see FIG. 11);
00/43/77/44/77/34/00/33/00 (see FIG. 12).

The intermediate bar can be threaded, one guide full, one guide empty, working in chain weave 10/01 or 01/10.

The front bar can be threaded full or in an arrangement with one yarn or with two yarns of different materials, originating from one reel or from two reels, and it can give one or other of the following weaves:

32/01 (see FIG. 13);
45/32/45/01/23/10 (see FIG. 14).

The prosthetic knit thereby obtained has the advantage of being self-fastening or self-gripping when turned back. The spiked naps can fasten onto the face of the knit which does not have spiked naps, by being turned back or by inverse superposition in place. This same prosthetic knit can be used for direct fastening in the tissues of the wall being treated, particularly when the spiked naps are made of absorbable yarn.

What is claimed is:

1. A prosthetic knit comprising an implantable tissue reinforcing knitted fabric having a first tissue gripping face including a plurality of spiked naps configured to directly fasten the knitted fabric to tissue, the spiked naps made of a bioabsorbable material and having a body and a head, the head having a greater width than the body and a generally spheroidal or mushroom shape.

2. A prosthetic knit as in claim 1 wherein the body of the spiked naps comprises a monofilament.

3. A prosthetic knit as in claim 1 wherein the body of the spiked naps comprises a monofilament made from polylactide.

4. A prosthetic knit as in claim 1 wherein the body of the spiked naps has a diameter of over 0.10 mm.

5. A prosthetic knit as in claim 1 wherein the spiked naps are present on the first face of the knitted fabric at a density between 50 and 90 naps per $cm^2$ of the knitted fabric.

6. A prosthetic knit as in claim 1 wherein the knitted fabric comprises open pores on the first face having a diameter of between 1 and 3 mm.

7. A prosthetic knit as in claim 1 wherein the knitted fabric comprises a plurality of sheets of interlaced yarns which together form a three-dimensional structure.

8. A prosthetic knit as in claim 1 wherein the knitted fabric comprises a monofilament yarn.

9. A prosthetic knit as in claim 1 wherein the knitted fabric comprises a multifilament yarn.

10. A prosthetic knit as in claim 1 wherein the knitted fabric comprises a bioabsorbable yarn.

11. A method comprising: (i) providing an implantable knitted fabric having a first tissue gripping face including a plurality of spiked naps, the spiked naps made of a bioabsorbable material and having a body and a head, the head having a greater width than the body and a generally spheroidal or mushroom shape, and (ii) positioning a portion of the first tissue gripping face into contact with tissue so that the spiked naps directly fasten the knitted fabric to the tissue.

12. The method of claim 11, wherein positioning the portion of the first tissue gripping face includes reinforcing a parietal defect in the tissue.

13. The prosthetic knit as in claim 1 wherein the body of the spiked naps has a length of between 1 mm and 2 mm.

14. The prosthetic knit as in claim 1 wherein the knitted fabric comprises a non-absorbable yarn.

15. The prosthetic knit as in claim 1 wherein the knitted fabric includes a second face having no spiked naps.

\* \* \* \* \*